(12) United States Patent
Kinoshita et al.

(10) Patent No.: US 10,130,270 B2
(45) Date of Patent: Nov. 20, 2018

(54) ELECTRONIC BLOOD PRESSURE MONITOR

(71) Applicant: OMRON HEALTHCARE CO., LTD., Muko-shi, Kyoto (JP)

(72) Inventors: Hiroyuki Kinoshita, Kyoto (JP); Hironori Sato, Kyoto (JP); Toshihiko Ogura, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 380 days.

(21) Appl. No.: 14/964,187

(22) Filed: Dec. 9, 2015

(65) Prior Publication Data

US 2016/0081565 A1    Mar. 24, 2016

Related U.S. Application Data

(63) Continuation of application No. PCT/JP2014/066192, filed on Jun. 18, 2014.

(30) Foreign Application Priority Data

Jul. 1, 2013  (JP) .................................. 2013-138150

(51) Int. Cl.
*A61B 5/022* (2006.01)
*A61B 5/00* (2006.01)

(52) U.S. Cl.
CPC .......... *A61B 5/02225* (2013.01); *A61B 5/742* (2013.01)

(58) Field of Classification Search
CPC combination set(s) only.
See application file for complete search history.

(56) References Cited

U.S. PATENT DOCUMENTS

2004/0087846 A1* 5/2004 Wasserman ........ A61B 5/04017
                                                600/323
2012/0203119 A1* 8/2012 Yamashita ......... A61B 5/02225
                                                600/490

FOREIGN PATENT DOCUMENTS

JP         H06-112 B2    1/1994
JP      2006-247216 A    9/2006
WO    WO 2011/052417  *  5/2011

OTHER PUBLICATIONS

Jul. 15, 2014 International Search Report issued in International Patent Application No. PCT/JP2014/066192.

(Continued)

*Primary Examiner* — Christian Jang
*Assistant Examiner* — Mitchell E Alter
(74) *Attorney, Agent, or Firm* — Oliff PLC

(57) ABSTRACT

An electronic blood pressure monitor retrieves a pulsewave signal that is superimposed on a cuff pressure signal and indicates a pulsewave at a measurement site, and acquires a string of pulsewave amplitudes indicated by the pulsewave signal. A first envelope connects the amplitudes created for the acquired string of pulsewave amplitudes. Local maxima and minima in the first envelope are detected. With respect to the strings of amplitudes corresponding respectively to the local maxima and minima, a local-maximum envelope and a local-minimum envelope connecting the amplitudes are created. Two pressure values at points at which portions on the high-pressure-side and low-pressure-side with respect to the maximum peaks of the local-maximum envelope and the local-minimum envelope respectively cross first and second threshold levels are obtained, and the average values of each pair of pressure values are calculated as the systolic blood pressure and the diastolic blood pressure respectively.

8 Claims, 13 Drawing Sheets

(56) References Cited

OTHER PUBLICATIONS

Jan. 5, 2016 Iternational Prelimanry Report on Pentability issued in International Patent Application No. PCT/JP2014/066192.

* cited by examiner

ELECTRONIC BLOOD PRESSURE MONITOR

TECHNICAL FIELD

This invention relates to electronic blood pressure monitors, and more specifically relates to an electronic blood pressure monitor that measures blood pressure at a measurement site using an oscillometric method.

BACKGROUND ART

Conventionally, as disclosed in Patent Document 1 (JP 2006-247216A) for example, as this kind of electronic blood pressure monitor that uses an oscillometric method, there is known to be an electronic blood pressure monitor that retrieves a pulsewave signal that is superimposed on a cuff pressure signal and indicates a pulsewave at a measurement site (upper arm, etc.), while changing the pressure of a cuff attached to the measurement site, and calculates blood pressure values (including systolic blood pressure and diastolic blood pressure, the same applies hereinafter) using an envelope for a string of amplitudes (pulsewave amplitudes) of the pulsewave signal with a predetermined algorithm. Specifically, an envelope that is smoothed using interpolation or the like is created in order to eliminate blood pressure measurement error that occurs due to error in the pulsewave amplitude accompanying respiratory blood pressure variation and bodily movement. Then, threshold levels are set on a high-pressure side and a low-pressure side with respect to the maximum peak of the envelope, and the pressures at the points at which the envelope crosses the threshold levels are respectively calculated as the systolic blood pressure and the diastolic blood pressure.

SUMMARY OF INVENTION

Technical Problem

Incidentally, blood pressure is not always constant, and it changes from moment to moment due to bodily factors, such as exercise and respiration, emotional factors such as stress and unease, external environmental factors such as temperature, or the like. In order to correctly measure blood pressure, it is recommended that measurement is performed in a resting state. However, even in a resting state, blood pressure variation that is synchronous with respiration (referred to as "respiratory variation") exists.

Here, the above-mentioned envelope includes such respiratory variation. As a result, the calculated blood pressure value is different depending on the respiratory period or the like, and there is a possibility that the calculated blood pressure will vary.

For example, FIGS. 13 and 14 show envelopes (original envelope before smoothing) $EV_O$ for a string of amplitudes of a pulsewave signal, and envelopes $EV_N$ that are smoothed using a moving average obtained by using the data of N points (N is a natural number) within a range of ±15 mmHg at each measurement point, in cases where the respiratory periods (i.e., periods of respiratory variation) are 4 seconds and 8 seconds, respectively. Threshold levels Ths and Thd are set on the high-pressure sides and low-pressure sides with respect to the maximum peaks of the envelopes. As can be understood from FIG. 13, if the respiratory period is 4 seconds, which is relatively fast, the envelope will include several instances of respiratory variation. As a result, the pressures at points Xs and Xd at which the smoothed envelope $EV_N$ crosses the threshold levels Ths and Thd correspond to the approximate centers of the points at which an upper-limit line $EV_U$ and a lower-limit line $EV_L$, which take into account the respiratory variation, crosses the threshold levels Ths and Thd. Accordingly, the calculated pressures represent the approximate average blood pressure values. In contrast, as can be understood from FIG. 14, if the respiratory period is 8 seconds, which is relatively slow, the envelope includes only one instance of respiratory variation (in this example, respiratory variation appears when the cuff pressure is about 100 mmHg). As a result, the pressures of points Xs' and Xd' at which the smoothed envelope $EV_N$ crosses the threshold levels Ths and Thd deviate from the centers of the points at which the upper-limit line $EV_U$ and the lower-limit line $EV_L$, which take the respiratory variation into account, cross the threshold levels Ths and Thd. For this reason, it cannot be said that the calculated pressures are the average blood pressure values.

Thus, with the conventional electronic blood pressure monitor, there is a possibility that the calculated blood pressure value will vary. For this reason, the current state of affairs is such that a measurement subject trying to find out his or her average blood pressure value will perform measurement multiple times. As a result, there is a problem in that blood pressure measurement is troublesome and is a significant burden to a measurement subject.

In view of this, the present invention aims to provide an electronic blood pressure monitor that can calculate an average blood pressure value taking respiratory variation into account.

Solution to Problem

In order to solve the foregoing problems, an electronic blood pressure monitor according to the invention is an electronic blood pressure monitor configured to measure blood pressure at a measurement site using an oscillometric method, the blood pressure monitor including:

a cuff pressure control unit that can change pressure in a cuff attached to a measurement site;

a pressure detection unit configured to detect a cuff pressure signal indicating the pressure in the cuff;

a pulsewave amplitude string acquisition unit configured to retrieve a pulsewave signal that is superimposed on the cuff pressure signal and indicates a pulsewave at the measurement site, and thereby acquire a string of amplitudes indicated by the pulsewave signal;

a first envelope creation unit configured to, with respect to the string of amplitudes acquired by the pulsewave amplitude string acquisition unit, create a first envelope connecting the amplitudes;

an extremum detection unit configured to detect local maxima and local minima in the first envelope;

a local-maximum envelope creation unit configured to, with respect to a string of amplitudes corresponding to the local maxima in the string of amplitudes acquired by the pulsewave amplitude string acquisition unit, create a local-maximum envelope connecting the amplitudes corresponding to the local maxima;

a local-minimum envelope creation unit configured to, with respect to a string of amplitudes corresponding to the local minima in the string of amplitudes acquired by the pulsewave amplitude string acquisition unit, create a local-minimum envelope connecting the amplitudes corresponding to the local minima;

a threshold level setting unit configured to, in order to obtain a systolic blood pressure and a diastolic blood pressure, calculate and set a first threshold level and a second threshold level that are respective percentages determined in advance with respect to a value of a maximum peak of the first envelope;

a systolic blood pressure calculation unit configured to obtain two pressure values at points at which portions on a high-pressure side with respect to maximum peaks of the local-maximum envelope and the local-minimum envelope cross the first threshold level, and calculate an average value of the two pressure values as systolic blood pressure; and a diastolic blood pressure calculation unit configured to obtain two pressure values at points at which portions on a low-pressure side with respect to maximum peaks of the local-maximum envelope and the local-minimum envelope cross the second threshold level, and calculate an average value of the two pressure values as diastolic blood pressure.

Here, the first envelope, the local-maximum envelope, and the local-minimum envelope are typically expressed using graphs in which cuff pressure is on the horizontal axis and pulsewave amplitude is on the vertical axis.

With the electronic blood pressure monitor of the invention, the cuff pressure control unit changes the pressure in a cuff attached to a measurement site during measurement. In the process of the pressure in the cuff increasing or decreasing, the pressure detection unit detects the cuff pressure signal, which indicates the pressure in the cuff. The pulsewave amplitude string acquisition unit retrieves a pulsewave signal that is superimposed on the cuff pressure signal and indicates a pulsewave at the measurement site, and thereby acquires a string of amplitudes indicated by the pulsewave signal. With respect to the string of amplitudes acquired by the pulsewave amplitude string acquisition unit, the first envelope creation unit creates a first envelope that connects the amplitudes. The extremum detection unit detects the local maxima and the local minima of the first envelope. With respect to the string of amplitudes corresponding to the local maxima in the string of amplitudes acquired by the pulsewave amplitude string acquisition unit, the local-maximum envelope creation unit creates a local-maximum envelope connecting the amplitudes corresponding to the local maxima. With respect to the string of amplitudes corresponding to the local minima in the string of amplitudes acquired by the pulsewave amplitude string acquisition unit, the local-minimum envelope creation unit creates a local-minimum envelope connecting the amplitudes corresponding to the local minima. In order to obtain the systolic blood pressure and the diastolic blood pressure, the threshold level setting unit calculates and sets a first threshold level and a second threshold level, which are respective percentages determined in advance with respect to the value of the maximum peak of the first envelope. The systolic blood pressure calculation unit obtains two pressure values (these are referred to as "two high-pressure-side pressure values" as appropriate) at points at which portions on the high-pressure-side with respect to the maximum peaks of the local-maximum envelope and the local-minimum envelope cross the first threshold level, and calculates the average value of the two pressure values as the systolic blood pressure. Also, the diastolic blood pressure calculation unit obtains two pressure values (these are referred to as "two low-pressure-side pressure values" as appropriate) at points at which portions on the low-pressure-side with respect to the maximum peaks of the local-maximum envelope and the local-minimum envelope cross the second threshold level, and calculates the average value of the two pressure values as the diastolic blood pressure.

Here, the difference between the local-maximum envelope and the local-minimum envelope includes respiratory variation. That is, the difference between the two high-pressure-side pressure values and the difference between the two low-pressure-side pressure values each include respiratory variation. Accordingly, it can be said that the average value of the two high-pressure-side pressure values calculated by the systolic blood pressure calculation unit as the systolic blood pressure and the average value of the two low-pressure-side pressure values calculated by the diastolic blood pressure calculation unit as the diastolic blood pressure are both average values that take respiratory variation into account. Thus, according to the electronic blood pressure monitor, an average blood pressure value taking respiratory variation into account can be calculated.

Furthermore, if the calculated blood pressure values (systolic blood pressure and diastolic blood pressure) are displayed on a display device (liquid crystal display, etc.) for example, the user (includes the measurement subject, the same applies hereinafter) can know the average blood pressure values that take the respiratory variation of the measurement subject into account. Accordingly, the measurement subject does not need to perform measurement multiple times. As a result, blood pressure measurement is easier for the measurement subject, and the burden can be reduced.

An electronic blood pressure monitor according to an embodiment includes a display device configured to display the calculated systolic blood pressure and diastolic blood pressure.

With the electronic blood pressure monitor according to the embodiment, by looking at the content displayed on the display device, the user can easily be made aware of the calculated systolic blood pressure and diastolic blood pressure, or in other words, average blood pressure values taking respiratory variation of the measurement subject into account.

An electronic blood pressure monitor according to an embodiment includes an envelope correction unit configured to correct the first envelope by removing a singularity from the string of amplitudes according to which the first envelope was created.

In the present specification, a "singularity" is defined as follows. If an amplitude value of interest in the string of amplitudes according to which the first envelope was created deviates by more than a predetermined reference from the values of the amplitudes aligned in front of and behind that amplitude, the amplitude of interest is a singularity.

Respiratory variation in blood pressure occurs periodically, synchronous with respiration, and appears as a trend in which several consecutive amplitudes in the string of amplitudes according to which the first envelope was created are larger or smaller. If the value of an amplitude of interest deviates by more than a predetermined reference from the values of amplitudes aligned in front of and behind that amplitude, the amplitude of interest is considered to be a non-periodic singularity caused by bodily movement of the measurement subject or the like during blood pressure measurement. In view of this, with the electronic blood pressure monitor according to the embodiment, the envelope correction unit corrects the first envelope by removing a singularity from the string of amplitudes according to which the first envelope was created. Accordingly, the extremum detection unit, the local-maximum envelope creation unit, the local-minimum envelope creation unit, and the threshold level setting unit perform the above-described processes using the corrected first envelope. Then, the systolic blood pressure calculation unit and the diastolic blood pressure calculation unit use the results of those processes to calculate the systolic blood pressure and the diastolic blood pressure, respectively. Accordingly, the precision of the calculated blood pressure value is increased.

An electronic blood pressure monitor according to an embodiment includes a smoothing unit configured to smooth the local-maximum envelope and the local-minimum envelope.

With the electronic blood pressure monitor according to the embodiment, the smoothing unit smooths the local-maximum envelope and the local-minimum envelope. Accordingly, the systolic blood pressure calculation unit calculates the systolic blood pressure using the smoothed local-maximum envelope and the smoothed local-minimum envelope. Also, the diastolic blood pressure calculation unit calculates the diastolic blood pressure using the smoothed local-maximum envelope and the smoothed local-minimum envelope. In such a case, the noise in the two high-pressure-side pressure values and the two low-pressure-side pressure values is reduced, and the precision of the calculated blood pressure values (the systolic blood pressure and the diastolic blood pressure) is increased.

Advantageous Effects of Invention

As is evident from the description above, according to an electronic blood pressure monitor of this invention, it is possible to calculate average blood pressure values that take respiratory variation into account.

DESCRIPTION OF EMBODIMENTS

Hereinafter, embodiments of the invention will be described in detail with reference to the drawings.

Figure 1:
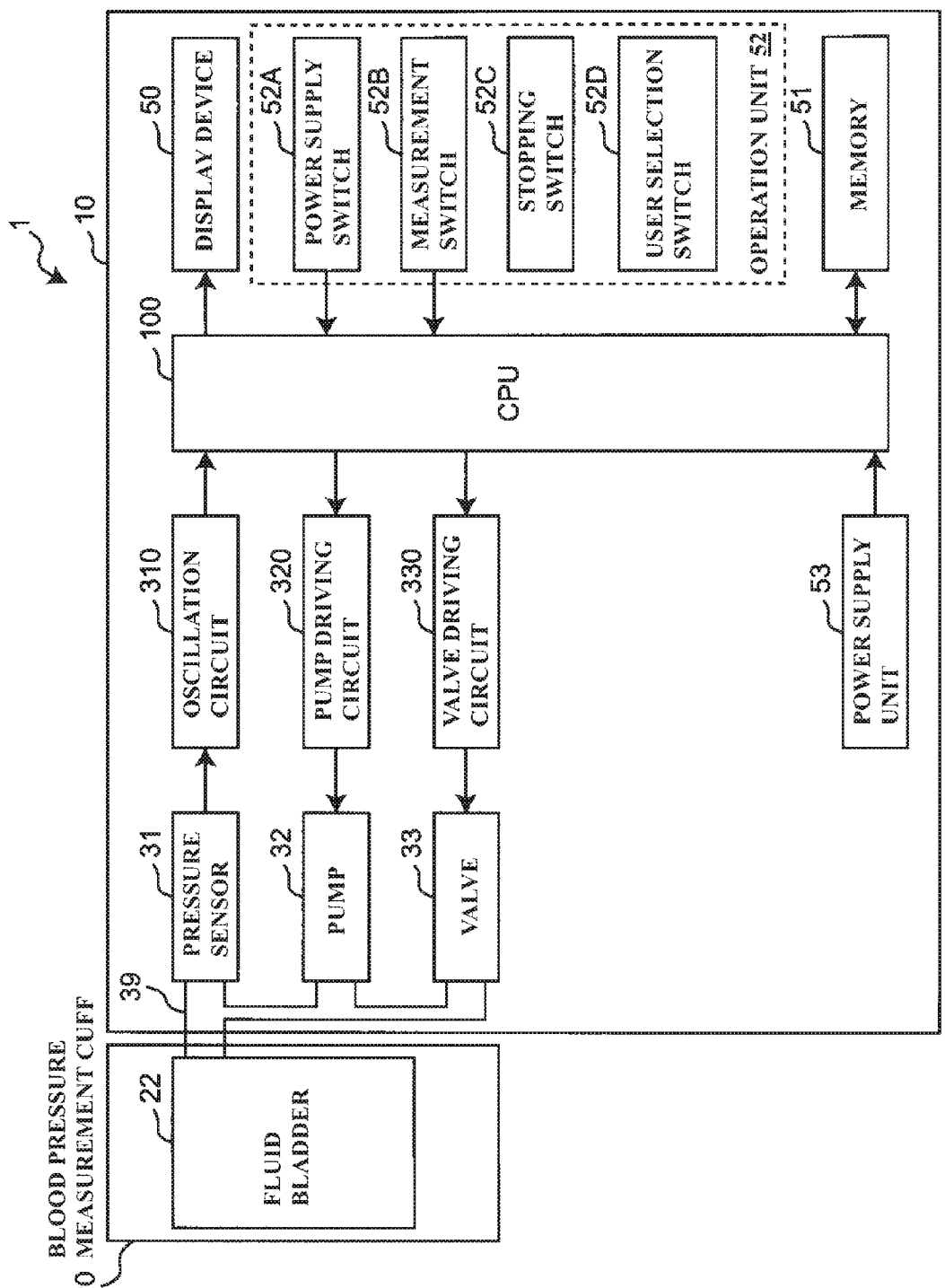
FIG. 1 is a diagram showing an overall block configuration of an electronic blood pressure monitor according to an embodiment of the invention.

FIG. 1 shows an overall block configuration of an electronic blood pressure monitor (indicated overall by reference numeral 1) according to an embodiment of the invention. The blood pressure monitor 1 includes a cuff 20, a main body 10, and a CPU (Central Processing Unit) 100 serving as a control unit, a display device 50, a memory 51 serving as a storage unit, an operation unit 52, a power supply unit 53, a pump 32, a valve 33, and a pressure sensor 31, which are mounted in the main body 10. Also, the main body 10 includes an oscillation circuit 310 that converts an output from the pressure sensor 31 into a frequency, a pump driving circuit 320 that drives the pump 32, and a valve driving circuit 330 that drives the valve 33, all of which are mounted in the main body 10.

The display device 50 includes a display, an indicator, and the like, and displays predetermined information in accordance with control signals from the CPU 100.

The operation unit 52 includes a power supply switch 52A that receives input of an instruction to turn on or turn off the power supply unit 53, a measurement switch 52B for receiving an instruction to start measurement of blood pressure, a stopping switch 52C for receiving an instruction to stop measurement, and a user selection switch 52D for selecting, from among multiple registered users, a user to be a measurement subject. The switches 52A, 52B, 52C, and 52D input operation signals corresponding to an instruction given by a user to the CPU 100.

The memory 51 stores data for programs for controlling the blood pressure monitor 1, data used for controlling the blood pressure monitor 1, setting data for setting various functions of the blood pressure monitor 1, data on results of measuring the blood pressure value, and the like. Also, the memory 51 is used as a working memory or the like for when a program is executed.

The CPU 100 functions as a cuff pressure control unit in accordance with a program for controlling the blood pressure monitor 1 that is stored in the memory 51, and performs control for driving the pump 32 and the valve 33 in response to operation signals from the operation unit 52. Also, the CPU 100 calculates the blood pressure values and controls the display device 50 and the memory 51 based on signals from the pressure sensor 31.

The power supply unit 53 supplies power to the CPU 100, the pressure sensor 31, the pump 32, the valve 33, the display device 50, the memory 51, the oscillation circuit 310, the pump driving circuit 320, and the valve driving circuit 330.

The pump 32 supplies air to a fluid bladder 22 contained in the cuff 20 in order to increase the pressure in the fluid bladder 22 (cuff pressure). The valve 33 is opened and closed in order to discharge or seal the air in the fluid bladder 22 and thereby control the cuff pressure. The pump driving circuit 320 drives the pump 32 based on a control signal provided from the CPU 100. The valve driving circuit 330 opens and closes the valve 33 based on a control signal provided from the CPU 100.

The pressure sensor 31 and the oscillation circuit 310 function as a pressure detection unit that detects the pressure in the cuff. The pressure sensor 31 is a piezoresistive pressure sensor, for example, and is connected via a cuff air tube 39 to the pump 32, the valve 33, and the fluid bladder 22 contained in the cuff 20. In this example, the oscillation circuit 310 oscillates based on an electric signal value that is from the pressure sensor 31 and is based on a change in electric resistance due to the piezoresistive effect, and outputs a frequency signal having a frequency corresponding to the electric signal value of the pressure sensor 31 to the CPU 100.

If blood pressure is to be measured in accordance with a common oscillometric method, the following operation is generally performed. That is, the cuff is wrapped around a measurement site (arm, etc.) of the measurement subject in advance, and during measurement, the pump and valve are controlled so as to increase the cuff pressure so that it is higher than the systolic blood pressure, and gradually reduce the cuff pressure thereafter. In the process of the pressure decreasing, the cuff pressure is detected by the pressure sensor, and changes in the arterial volume that occur in the artery at the measurement site are retrieved as a pulsewave signal. The systolic blood pressure and the diastolic blood pressure are calculated based on changes in the amplitude of the pulsewave signal that accompany changes in the cuff pressure at this time (mainly rising edges and falling edges).

Figure 2:
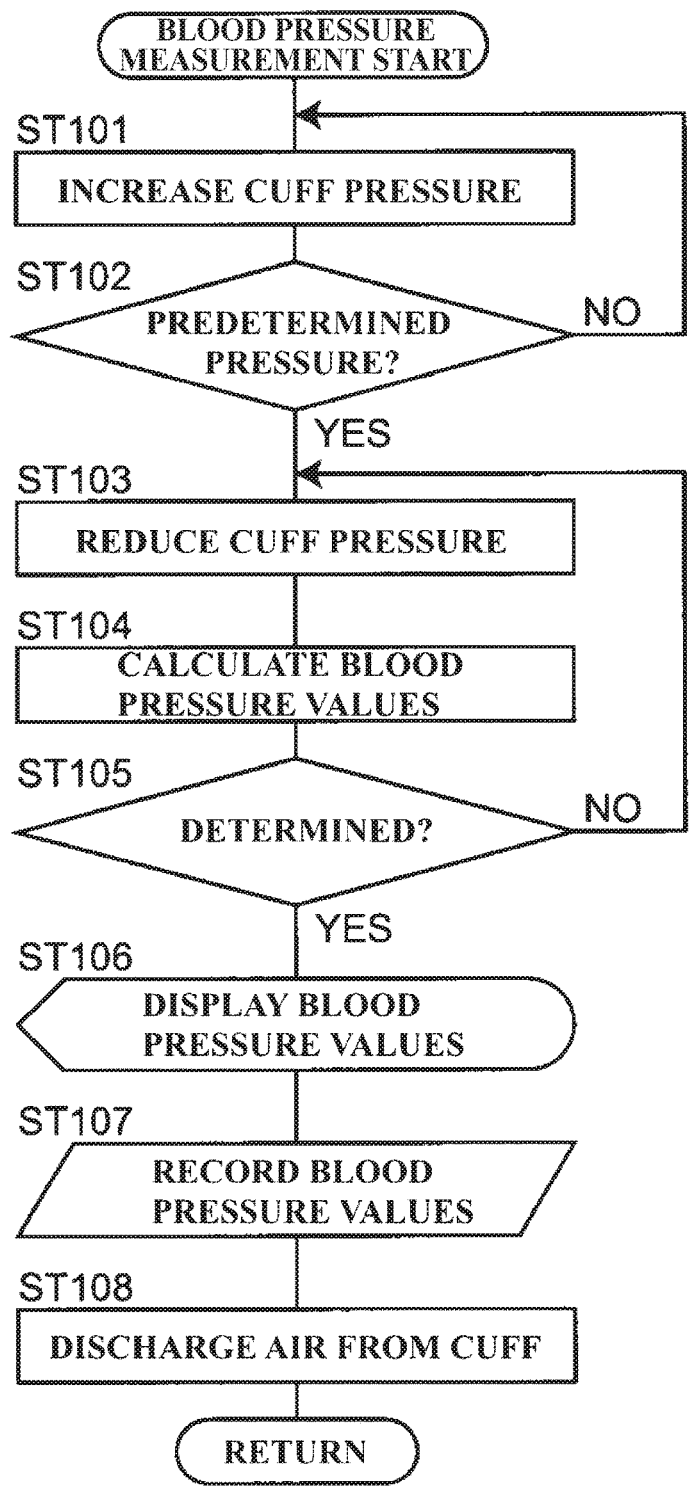
FIG. 2 is a diagram showing an overall operation flow of the electronic blood pressure monitor.

With the blood pressure monitor 1, the blood pressure values of a measurement subject are measured by the CPU 100 using an oscillometric method in accordance with the flow in FIG. 2.

Specifically, when the measurement switch 52B is pressed while the power supply switch 52A is on, the blood pressure monitor 1 starts blood pressure measurement, as shown in FIG. 2. When blood pressure measurement is started, the CPU 100 initializes the memory region for processing, and outputs a control signal to the valve driving circuit 330. Based on the control signal, the valve driving circuit 330 opens the valve 33 so as to discharge the air in the fluid bladder 22 of the cuff 20. Next, control for adjusting the pressure sensor 31 to 0 mmHg is performed.

When blood pressure measurement is started, the CPU 100 first closes the valve 33 via the valve driving circuit 330 and then drives the pump 32 via the pump driving circuit 320, thereby performing control for sending air to the fluid bladder 22. Accordingly, the fluid bladder 22 is inflated and the cuff pressure gradually increases (step ST101).

When the cuff pressure is increased to a predetermined pressure (YES in step ST102), the CPU 100 stops the pump 32 via the pump driving circuit 320, and then performs control for gradually opening the valve 33 via the valve driving circuit 330. Accordingly, the fluid bladder 22 is deflated and the cuff pressure gradually decreases (step ST103).

Here, the predetermined pressure is a pressure that is sufficiently higher than the systolic blood pressure of the measurement subject (e.g., systolic blood pressure+30 mmHg), and it is stored in advance in the memory 51 or it is determined by the CPU 100 estimating the systolic blood pressure using a predetermined calculation equation while the cuff pressure is increased (e.g., see JP 2001-70263A).

Also, as for the pressure decrease rate, a target pressure decrease rate that is to be a target is set while the cuff is being inflated, and the CPU 100 controls the degree of opening of the valve 33 so as to reach the target pressure decrease rate (see JP 2001-70263A).

In the pressure decrease process, the cuff pressure signal (indicated by reference sign Pc) representing the pressure in the cuff 20 is detected by the pressure sensor 31 via the cuff 20. Based on the cuff pressure signal Pc, the CPU 100 calculates the blood pressure values (systolic blood pressure and diastolic blood pressure) by applying a later-described algorithm using an oscillometric method (step ST104). Note that the calculation of the blood pressure values is not limited to the pressure decrease process and may be performed in the pressure increase process.

When the blood pressure values are calculated and determined (YES in step ST105), the CPU 100 performs control for displaying the calculated blood pressure values on the display device 50 (step ST106) and storing the blood pressure values in the memory 51 (step ST107).

Next, when the stopping switch 52C is pressed, the CPU 100 performs control for opening the valve 33 via the valve driving circuit 330 and discharges the air in the fluid bladder 22 of the cuff 20 (step ST108).

When the power supply switch 52A is pressed thereafter, blood pressure measurement is ended.

First Example

Figure 3:
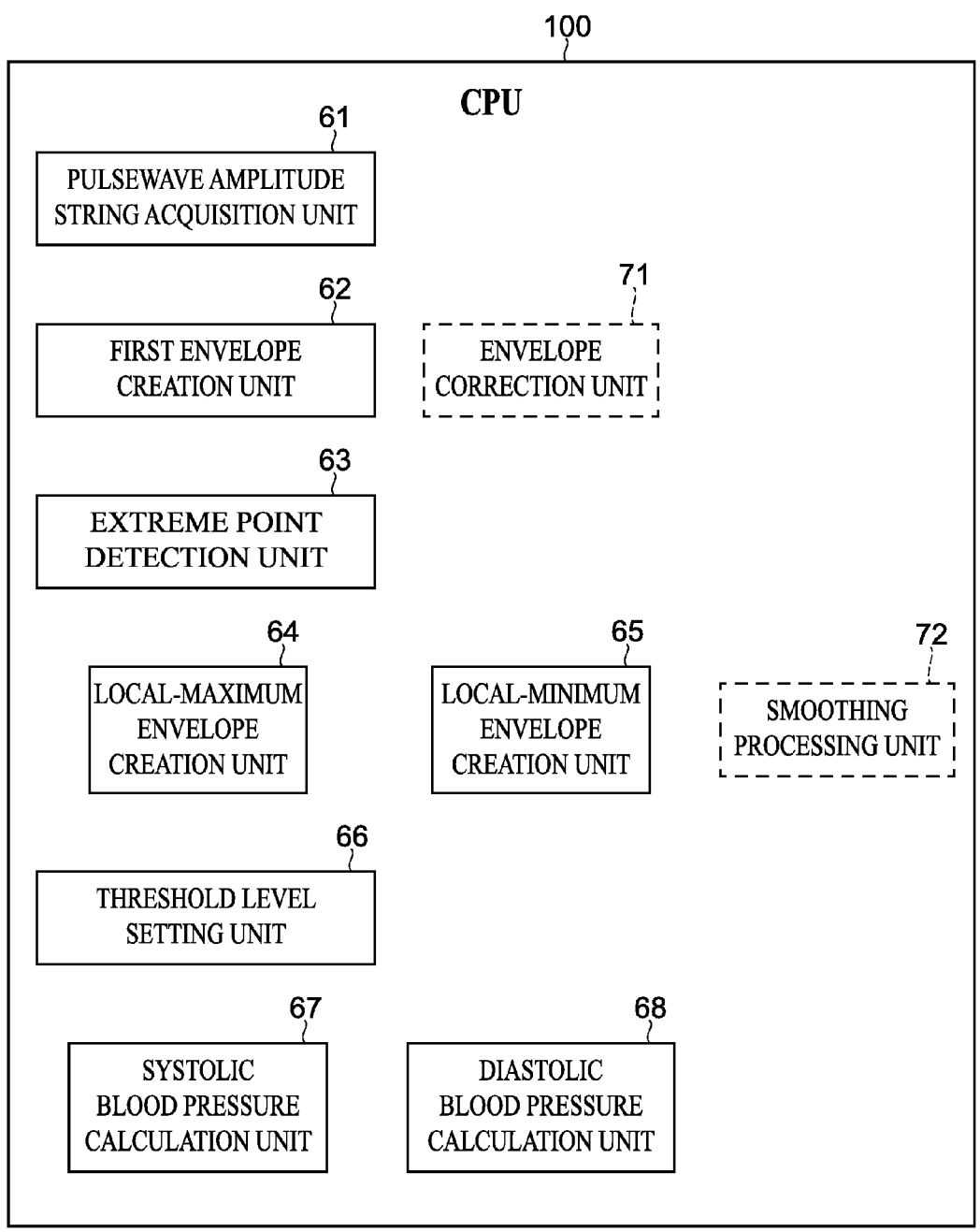
FIG. 3 is a diagram illustrating a set of elements included in a CPU (Central Processing Unit) of the electronic blood pressure monitor in order to calculate blood pressure values.
Figure 4:
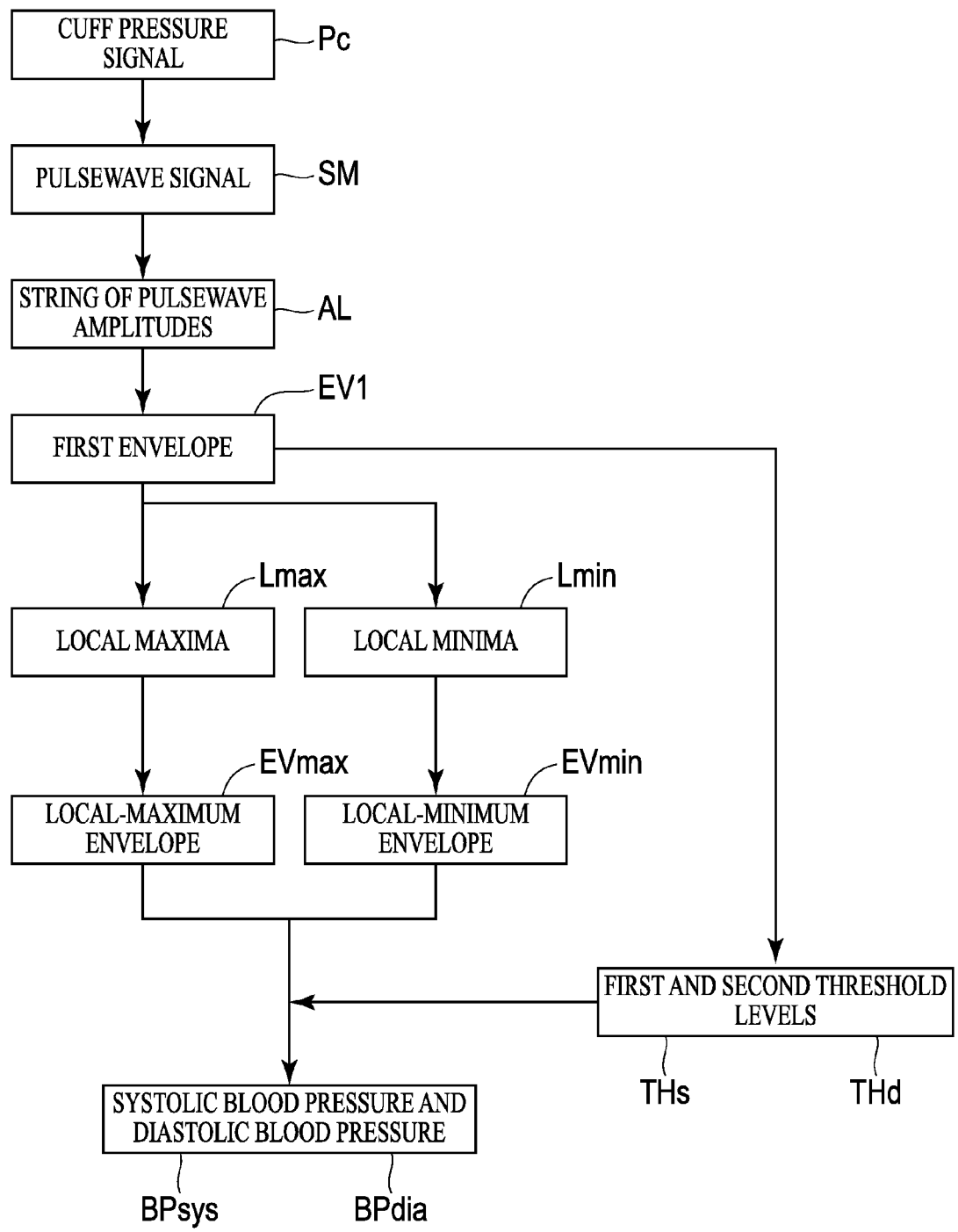
FIG. 4 is a diagram for illustrating processing for when blood pressure values are calculated by a portion of the elements in FIG. 3.

FIG. 3 illustrates elements included in the CPU 100 (software) of the electronic blood pressure monitor 1, in order to calculate the blood pressure values. In the first example, the elements for calculating the blood pressure values include a pulsewave amplitude string acquisition unit 61, a first envelope creation unit 62, an extremum detection unit 63, a local-maximum envelope creation unit 64, a local-minimum envelope creation unit 65, a threshold level setting unit 66, a systolic blood pressure calculation unit 67, and a diastolic blood pressure calculation unit 68. FIG. 4 shows a flow of processing for when the blood pressure values are calculated by the elements in FIG. 3. Note that in the first example, an envelope correction unit 71 and a smoothing processing unit 72 indicated by the frames with broken lines in FIG. 3 are excluded.

A method of calculating the blood pressure values based on a cuff pressure signal Pc will be described mainly with reference to FIGS. 3 and 4.

i) First, as shown in FIG. 4, the pulsewave amplitude string acquisition unit 61 shown in FIG. 3 receives the cuff pressure signal Pc detected by the above-described pressure sensor 31 and retrieves a pulsewave signal SM that indicates a pulsewave at the measurement site, which is superimposed on the cuff pressure signal Pc.

Figure 5A:
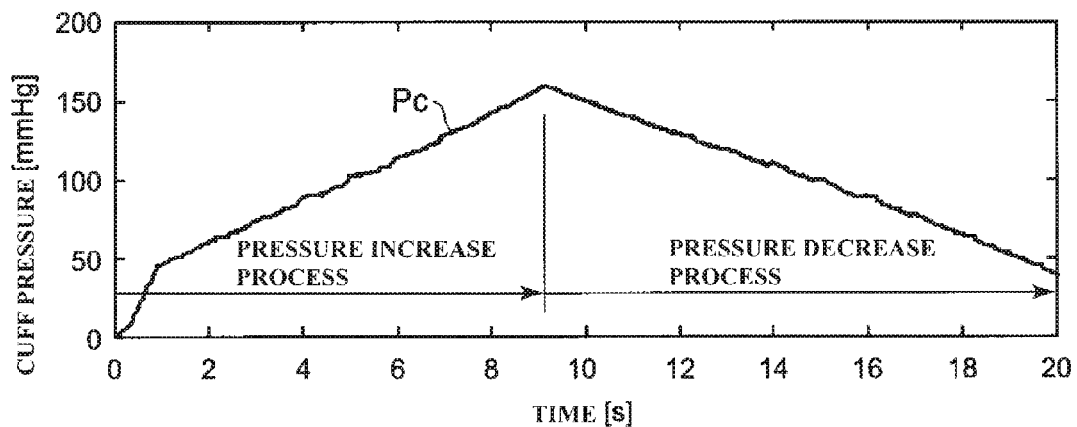
FIG. 5(A) is a diagram illustrating a cuff pressure signal detected via a pressure sensor of the electronic blood pressure monitor.
Figure 5B:
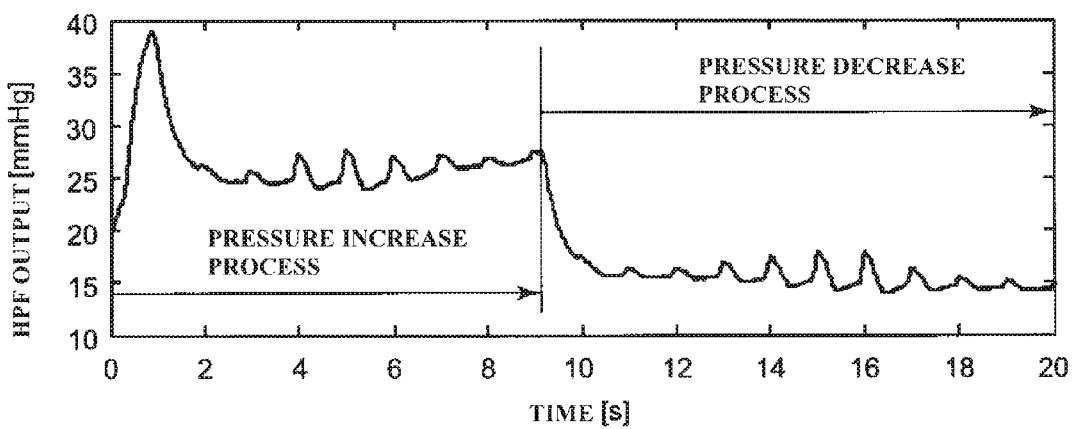
FIG. 5(B) is a diagram illustrating a signal (HPF output) retrieved from the cuff pressure signal via a high-pass filter.
Figure 6:
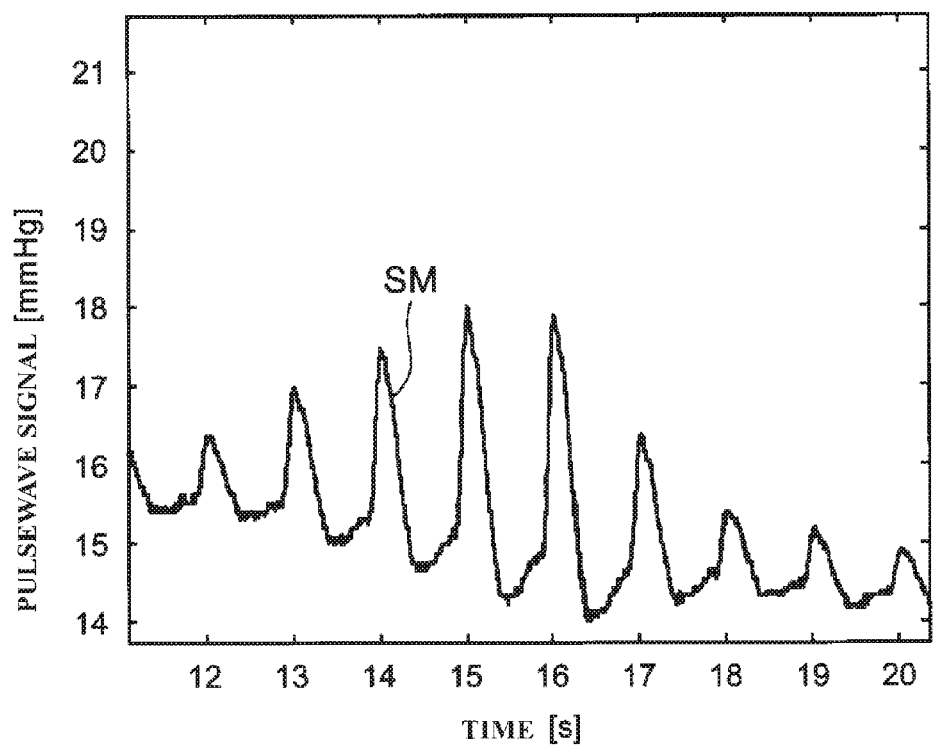
FIG. 6 is a diagram illustrating the signal in FIG. 5(B) as an enlarged pulsewave signal representing a pulsewave at the measurement site in the pressure decrease process.

Here, as shown in FIG. 5(A), the cuff pressure signal Pc is a signal in which a variation component accompanying changes in artery volume for each heartbeat is superimposed on the pressure that rises (pressure increase process) or falls (pressure decrease process) almost linearly as time elapses. The pulsewave amplitude string acquisition unit 61 retrieves a variation component (HPF output) such as that shown in FIG. 5(B) from the cuff pressure signal Pc via a high-pass filter (HPF), and outputs it as a pulsewave signal SM such as that shown in FIG. 6. In this example, as shown in FIG. 6 (corresponds to the pressure decrease process), according to the variation in the arterial volume, the pulsewave signal SM starts to increase about 12 seconds from the start of measurement, reaches its maximum about 16 seconds from the start of measurement, and mostly dissipates about 20 seconds from the start of measurement.

Figure 7:
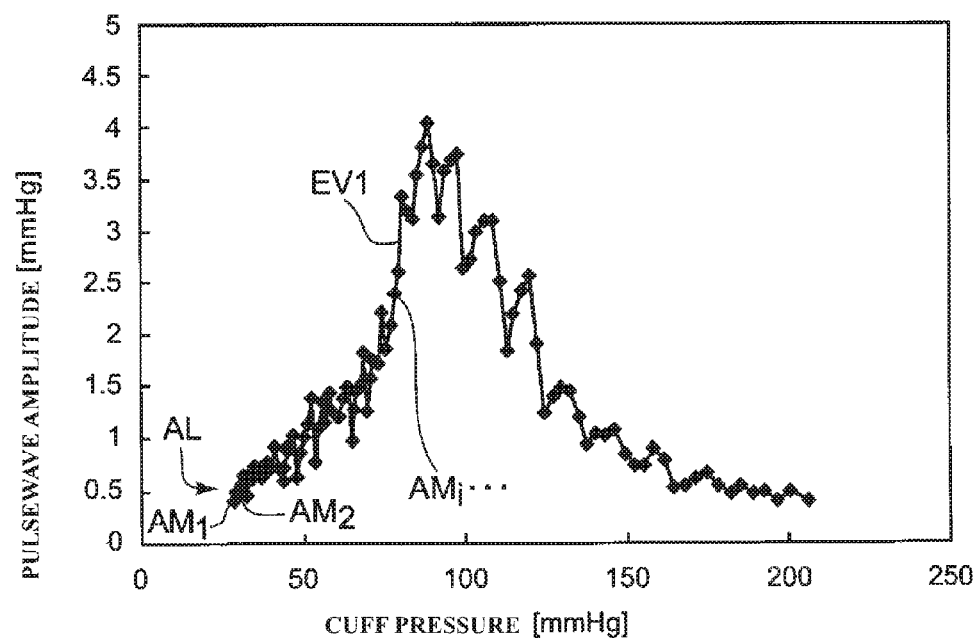
FIG. 7 is a diagram showing a string of amplitudes indicated by the pulsewave signal, and a first envelope created according to the string of amplitudes.

Also, the pulsewave amplitude column acquisition unit 61 acquires an amplitude (hereinafter referred to as "pulsewave amplitude" as appropriate) string AL indicated by the pulsewave signal SM. In this example, as shown in FIG. 7, the pulsewave amplitude string AL is shown as the string AL of amplitudes (peak values) $AM_1, AM_2, \ldots, AM_i, \ldots$ for each heartbeat, with the cuff pressure on the horizontal axis.

ii) Next, as shown in FIG. 4, with respect to the pulsewave amplitude string AL acquired by the pulsewave amplitude string acquisition unit 61, the first envelope creation unit 62 in FIG. 3 creates a first envelope EV1 that connects the amplitudes. Here, the first envelope EV1 has peaks and troughs caused by respiratory variation, as shown in FIG. 7.

Figure 8:
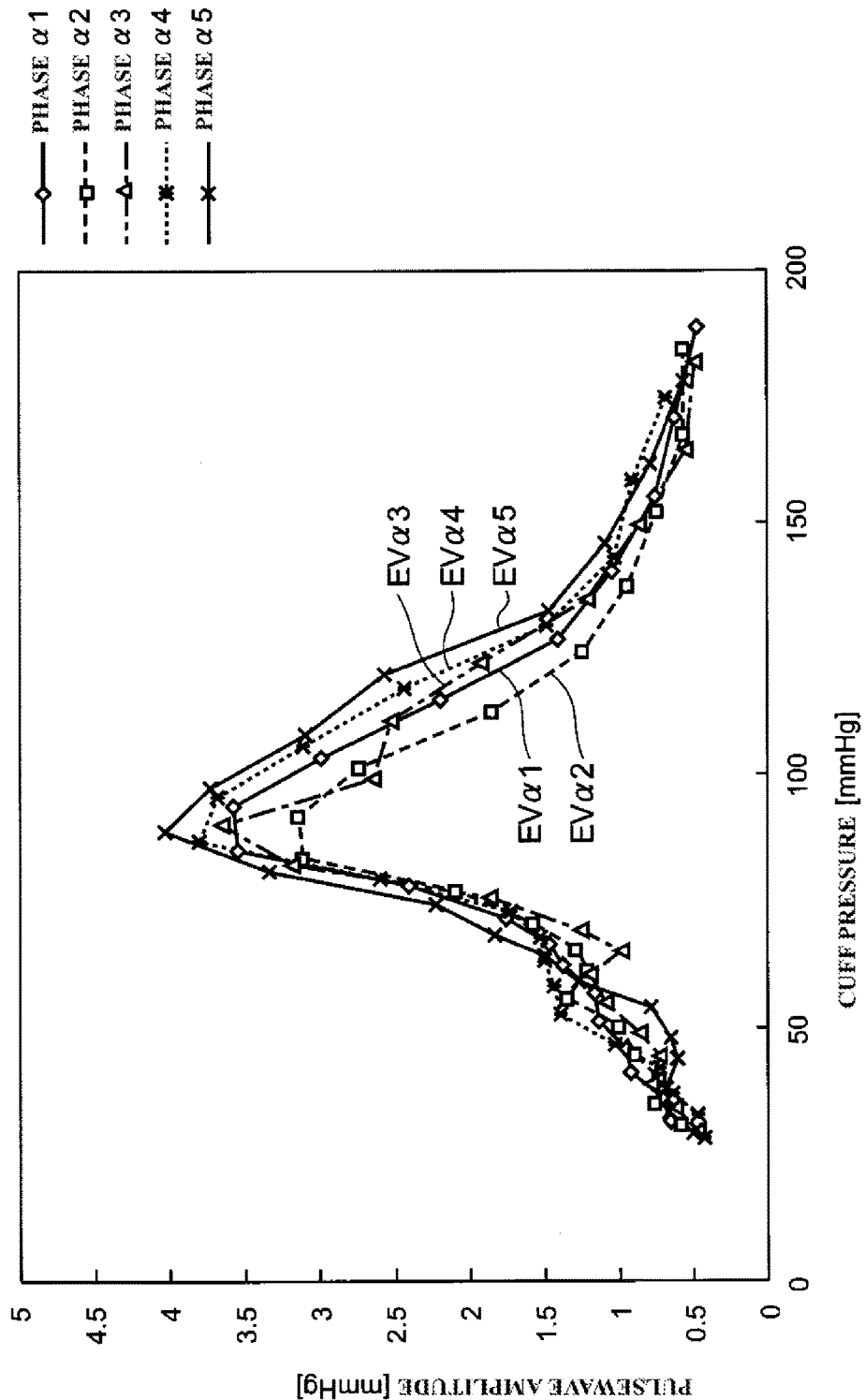
FIG. 8 is a diagram showing an example in which, in a case where the respiratory period of the measurement subject is known, a string of amplitudes is acquired from the pulsewave signal for each phase of the respiratory period, and envelopes are created for the amplitude string of each phase.
Figure 9:
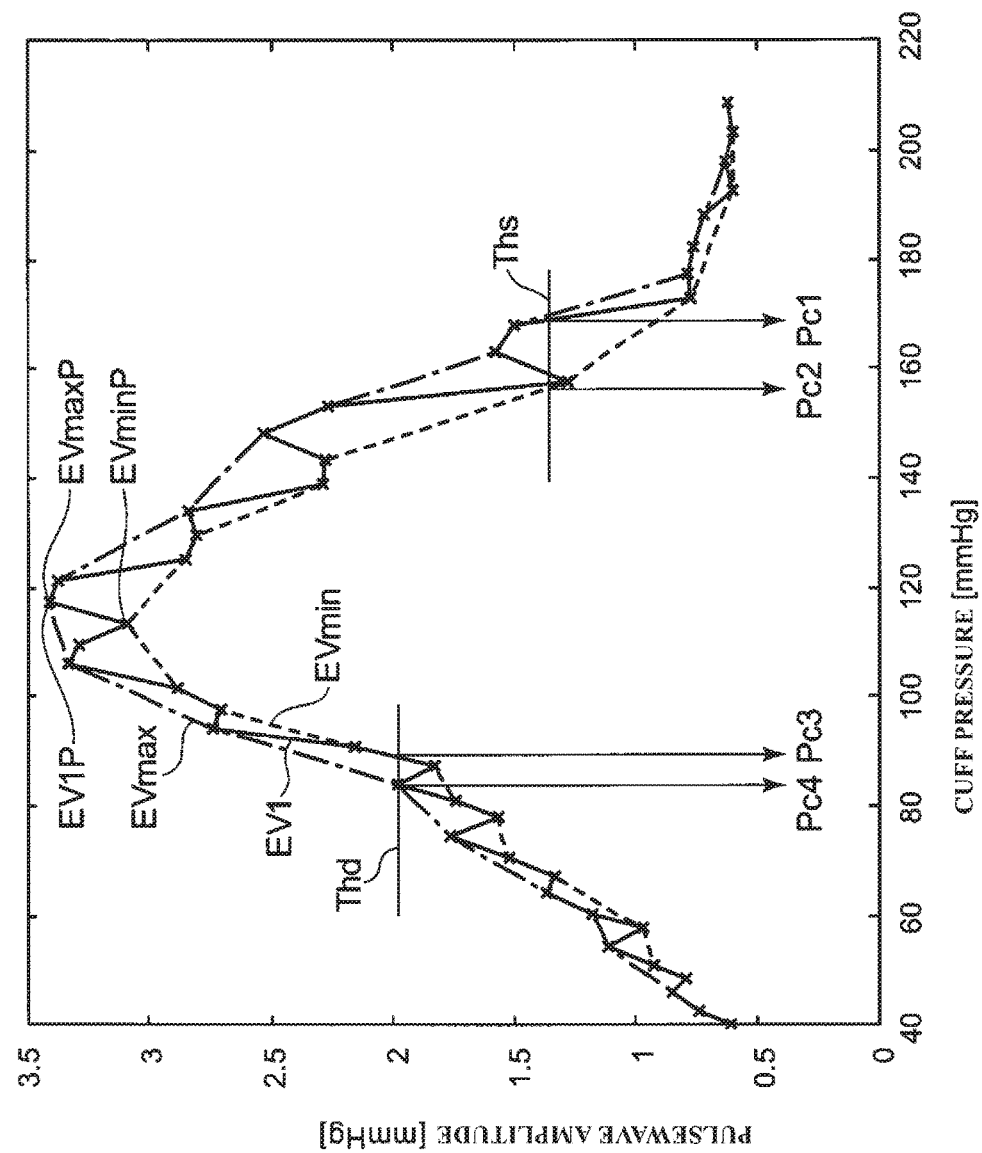
FIG. 9 is a diagram showing a method of calculating systolic blood pressure and diastolic blood pressure using a local-maximum envelope and a local-minimum envelope.

For reference, FIG. 8 shows an example in which, in the case where the respiratory period of the measurement subject is known, an amplitude string is acquired for each phase $\alpha 1, \alpha 2, \ldots, \alpha 5$ of the respiratory period from the pulsewave amplitude string AL of the pulsewave signal SM, and envelopes $EV\alpha 1, EV\alpha 2, \ldots EV\alpha 5$ are created respectively for the amplitude strings for the phases $\alpha 1, \alpha 2, \ldots, \alpha 5$. The phases $\alpha 1, \alpha 2, \ldots, \alpha 5$ each differ by 60°, with one respiratory period being 360°. In the example shown in FIG. 8, $EV\alpha 5$ corresponds to an envelope for when the respiratory variation is at local maxima, and $EV\alpha 2$ corresponds to an envelope for when the respiratory variation is at local minima. In order to obtain an average blood pressure value, the envelope for when the respiratory variation is at local maxima and the envelope for when the respiration variation is at local minima can be thought of respectively as an upper-limit line and a lower-limit line taking the respiratory variation into account.

iii) In view of this, as shown in FIG. 4, the extremum detection unit 63 in FIG. 3 detects local maxima Lmax and local minima Lmin in the first envelope EV1. The local maxima Lmax and the local minima Lmin are each a string of multiple points.

iv) Next, the local-maximum envelope creation unit 64 shown in FIG. 3 creates a local-maximum envelope EVmax that connects the amplitudes of, in the pulsewave amplitude string AL acquired by the pulsewave amplitude string acquisition unit 61, the string of amplitudes corresponding to the local maxima Lmax, as shown in FIG. 9. On the other hand, the local-minimum envelope creation unit 65 shown in FIG. 3 creates a local-minimum envelope EVmin that connects the amplitudes of, in the pulsewave amplitude string AL acquired by the pulsewave amplitude string acquisition unit 61, the string of amplitudes corresponding to the local minima Lmin, as shown in FIG. 9.

v) Also, in order to obtain the systolic blood pressure BPsys and the diastolic blood pressure BPdia, the threshold level setting unit 66 shown in FIG. 3 calculates and sets a first threshold level Ths and a second threshold level Thd, which are respective percentages determined in advance with respect to the value of the maximum peak EV1P of the first envelope EV1. In this example, the first threshold level Ths is set to 40% of the value of the maximum peak EV1P, and the second threshold level Thd is set to 50% of the value of the maximum peak EV1P.

vi) Next, the systolic blood pressure calculation unit 67 shown in FIG. 3 obtains two pressure values Pc1 and Pc2 at the points at which the portions on the high-pressure side with respect to the maximum peaks EVmaxP and EVminP of the local-maximum envelope EVmax and the local-minimum envelope EVmin cross the first threshold level Ths, and calculates the average value of the two pressure values, or (Pc1+Pc2)/2, as the systolic blood pressure BPsys, as shown in FIGS. 4 and 9. Also, the diastolic blood pressure calculation unit 68 shown in FIG. 3 obtains two pressure values Pc3 and Pc4 at the points at which the portions on the low-pressure side with respect to the maximum peaks EVmaxP and EVminP of the local-maximum envelope EVmax and the local-minimum envelope EVmin cross the second threshold level Thd, and calculates the average value of the two pressure values, or (Pc3+Pc4)/2, as the diastolic blood pressure BPdia, as shown in FIGS. 4 and 9.

Here, the local-maximum envelope EVmax and the local-minimum envelope EVmin respectively correspond to the upper-limit line and the lower-limit line of the respiratory variation. Accordingly, it can be said that the average value of the two high-pressure-side pressure values, or (Pc1+Pc2)/2, and the average value of the two low-pressure-side pressure values, or (Pc3+Pc4)/2, are average values that take the respiratory variation into account. Thus, according to the electronic blood pressure monitor 1, average blood pressure values that take respiratory variation into account can be calculated.

Furthermore, the calculated blood pressure values (systolic blood pressure BPsys and diastolic blood pressure BPdia) are displayed on the display device 50. Accordingly, the user can find out the average blood pressure values that take the measurement subject's respiratory variation into account. Accordingly, the measurement subject does not need to perform measurement multiple times. As a result, blood pressure measurement is easier for the measurement subject, and the burden is reduced.

In the above example, the first threshold level Ths was set to be 40% of the value of the maximum peak EV1P and the second threshold level Thd was set to be 50% of the value of the maximum peak EV1P, but there is no limitation to this. For example, the percentages of the threshold levels with respect to the value of the maximum peak EV1P may be changed such that the first threshold level Ths is set to be 50% of the value of the maximum peak EV1P, and the second threshold level Thd is set to be 70% of the value of the maximum peak EV1P. Also, instead of setting the threshold level percentages using the value of the maximum peak EV1P in the first envelope EV1 as the reference, it is possible to set the threshold level percentages using the value of the maximum peak EVmaxP of the local-maximum envelope EVmax or the value of the maximum peak EVminP of the local-minimum envelope EVmin as the reference.

Also, if the difference between the two high-pressure-side pressure values Pc1 and Pc2 (Pc1−Pc2) exceeds a predetermined percentage (e.g., being set in a range from around 2-3% to 10%) with respect to the calculated systolic blood pressure BPsys, or if the difference between the low-pressure-side pressure values Pc3 and Pc4 (Pc3−Pc4) exceeds a predetermined percentage (e.g., being set in a range from around 2-3% to 10%) with respect to the calculated diastolic blood pressure BPdia, the CPU 100 may perform notification by displaying the calculated blood pressure values (systolic blood pressure BPsys and diastolic blood pressure BPdia) and a message saying "Because blood pressure variation is large, re-measurement is recommended" on the display device 50.

Also, in addition to displaying such a message, or instead of displaying the message, it is possible to perform notification of this using an alarm sound, for example.

With this kind of notification, the user can easily be made aware of the fact that there is a possibility that measurement was not performed correctly and it is therefore necessary to perform re-measurement after some time has passed.

Second Example

In the second example, the blood pressure value is calculated using all of the elements shown in FIG. 3. That is to say, the envelope correction unit 71 and the smoothing processing unit 72 shown in the frames with broken lines in FIG. 3 function in addition to the pulsewave amplitude string acquisition unit 61, the first envelope creation unit 62, the extremum detection unit 63, the local-maximum envelope creation unit 64, the local-minimum envelope creation unit 65, the threshold level setting unit 66, the systolic blood pressure calculation unit 67, and the diastolic blood pressure calculation unit 68, which have already been described in the first example.

Figure 10:
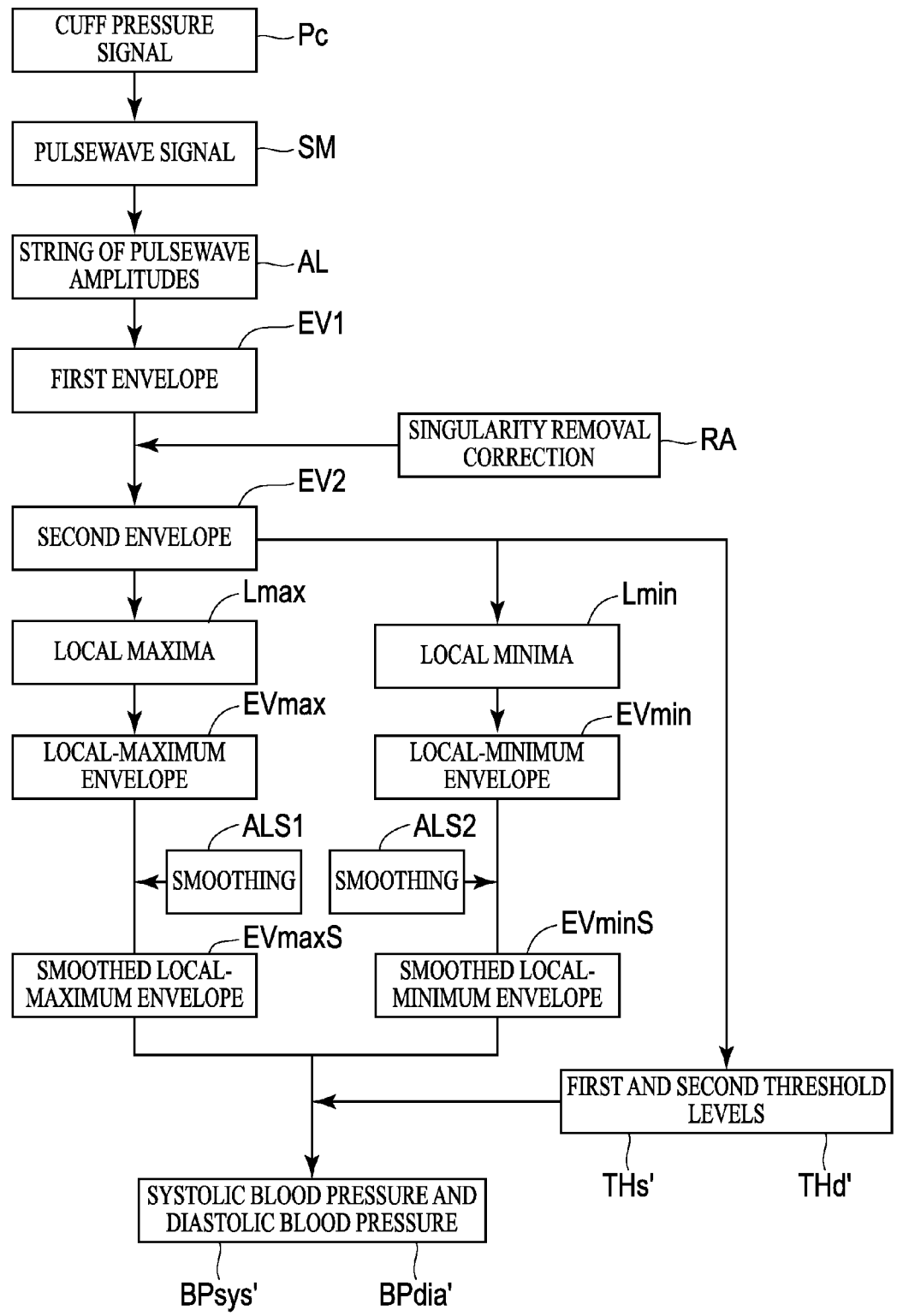
FIG. 10 is a diagram for illustrating processing for when blood pressure values are calculated by all of the elements in FIG. 3.
Figure 11:
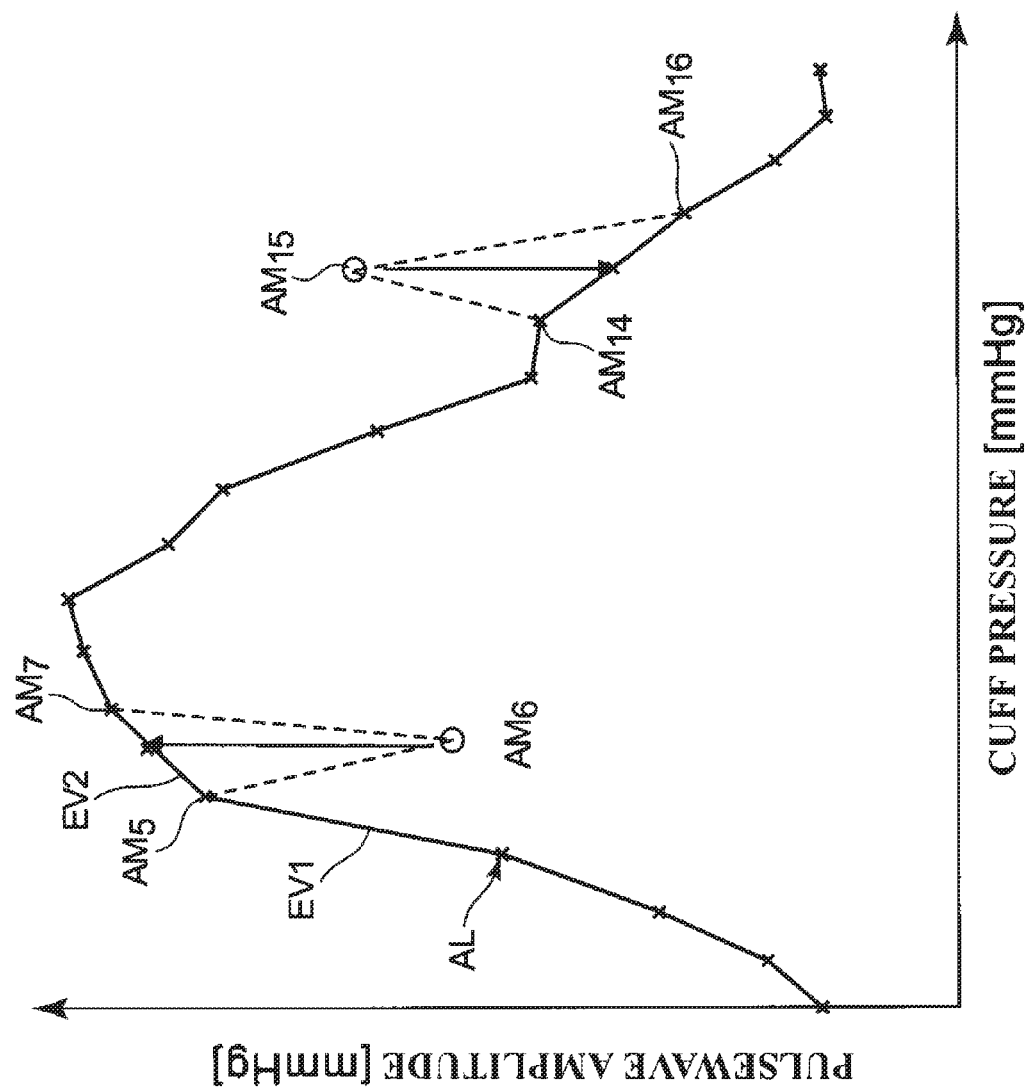
FIG. 11 is a diagram showing a correction method for removing singularities from a string of amplitudes according to which a first envelope is created.

FIG. 10 shows a flow of processing for when the blood pressure value is calculated using all of the elements shown in FIG. 3. The processing of FIG. 10 includes a flow that is roughly similar to the processing of FIG. 4. The processing of FIG. 10 is different in that processing in which the envelope correction unit 71 performs correction (singularity removal correction) RA for removing singularities from the amplitude string AL according to which the first envelope EV1 is created, and processing in which the smoothing processing unit 72 performs smoothing ALS1 and ALS2 on the local-maximum envelope EVmax and the local-minimum envelope EVmin are added. Hereinafter, for the sake of convenience, description that is redundant with that of the first example will not be given, and only differences from the first example will be described.

i) FIG. 11 illustrates a method of correction (singularity removal correction) RA in which singularities are removed from the amplitude string AL according to which the first envelope EV1 was created. The singularity removal correction RA is for removing, from the first envelope EV1, non-periodic components that are different from respiratory variation and are caused by bodily movement of the measurement subject during blood pressure measurement.

In this example, in the amplitude string AL according to which the first envelope EV1 was created, when the value of an amplitude of interest (referred to as $AM_i$) deviates by more than a predetermined reference from the values of the amplitudes aligned in front of and behind that amplitude (referred to as $AM_{i-1}$ and $AM_{i+1}$), the amplitude of interest $AM_i$ is defined as a singularity. Specifically, the following three equations are used to determined whether or not each point corresponding to an amplitude is a singularity. First, the amplitude $AM_i$ is assumed to be a singularity if the amplitude $AM_i$ satisfies the following equation:

$$AM_i < (AM_{i-1} + AM_{i+1})/4 \quad (1)$$

The right side of equation (1) means 0.5 times the average value of the preceding and following amplitudes $AM_{i-1}$ and $AM_{i+1}$.

Also, the amplitude $AM_i$ is assumed to not be a singularity if the amplitude $AM_i$ satisfies the following equation:

$$(AM_{i-1} + AM_{i+1})/4 < AM_i \leq 3(AM_{i-1} + AM_{i+1})/4 \quad (2)$$

The right side of equation (2) means 1.5 times the average value of the preceding and following amplitudes $AM_{i-1}$ and $AM_{i+1}$.

Also, the amplitude $AM_i$ is assumed to be a singularity if the amplitude $AM_i$ satisfies the following equation:

$$3(AM_{i-1} + AM_{i+1})/4 < AM_i \quad (3)$$

In the example shown in FIG. 11, since amplitude $AM_6$ is such that $AM_6 < (AM_5 + AM_7)/4$, which satisfies equation (1), it is determined that amplitude $AM_6$ is a singularity. Also, since amplitude $AM_{15}$ is such that $3(AM_{14} + AM_{16})/4 < AM_{15}$, which satisfies equation (3), it is determined that amplitude $AM_{15}$ is a singularity. On the other hand, it is determined that the remaining amplitudes in the amplitude string AL are not singularities.

In this example, when it is determined that an amplitude $AM_i$ is a singularity, the amplitude $AM_i$ is replaced with the average value $(AM_{i-1} + AM_{i+1})/2$ of the amplitudes $AM_{i-1}$ and $AM_{i+1}$, which are aligned in front of and behind the amplitude $AM_i$ and thereby the first envelope EV1 is corrected to be smooth (interpolation). Note that the amplitude $AM_i$ may simply be removed. In FIGS. 10 and 11, the envelope resulting from the singularity removal correction RA is shown as a second envelope EV2.

Figure 12:
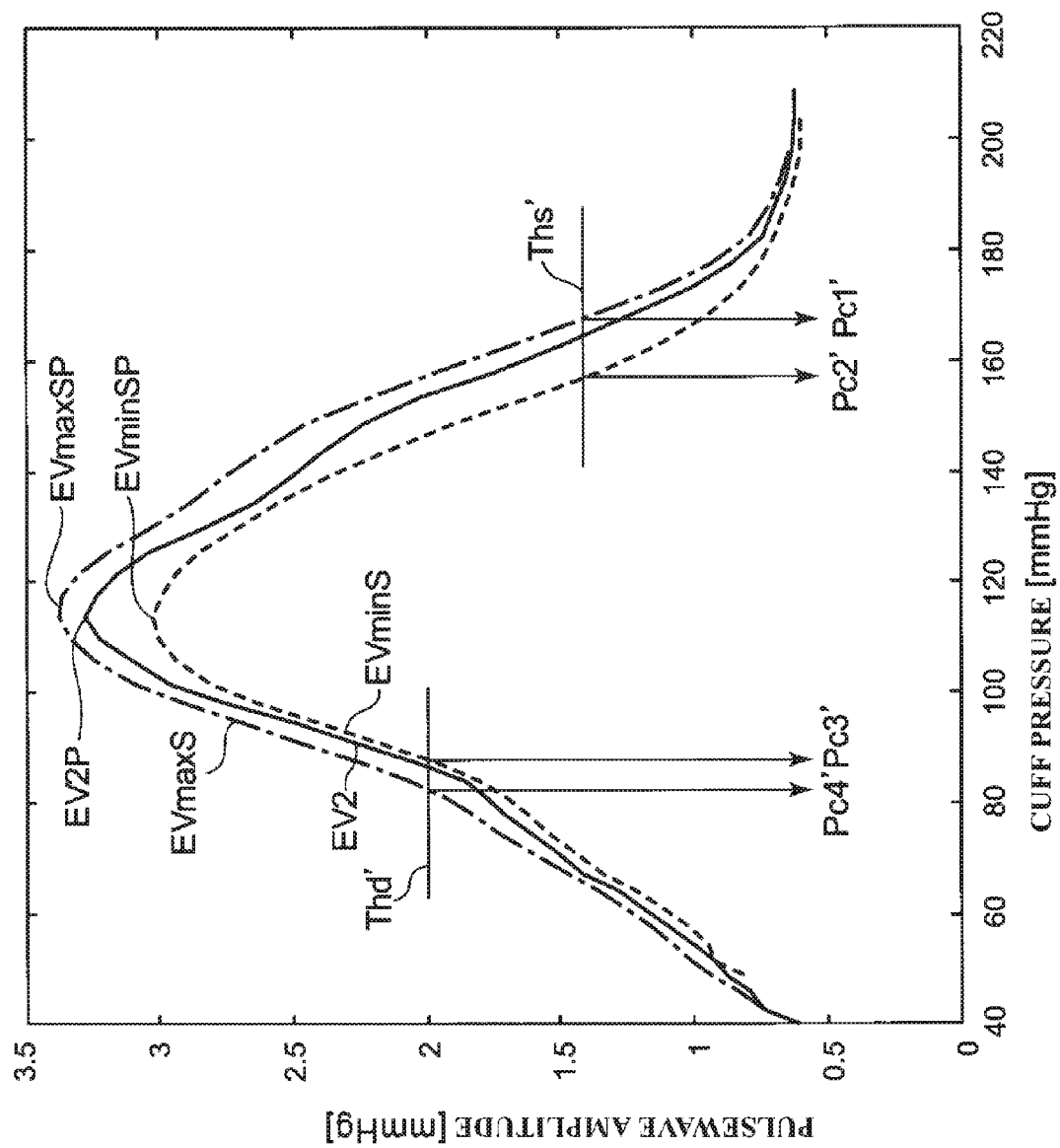
FIG. 12 is a diagram showing a method of calculating systolic blood pressure and diastolic blood pressure using a smoothed local-maximum envelope and a smoothed local-minimum envelope.
Figure 13:
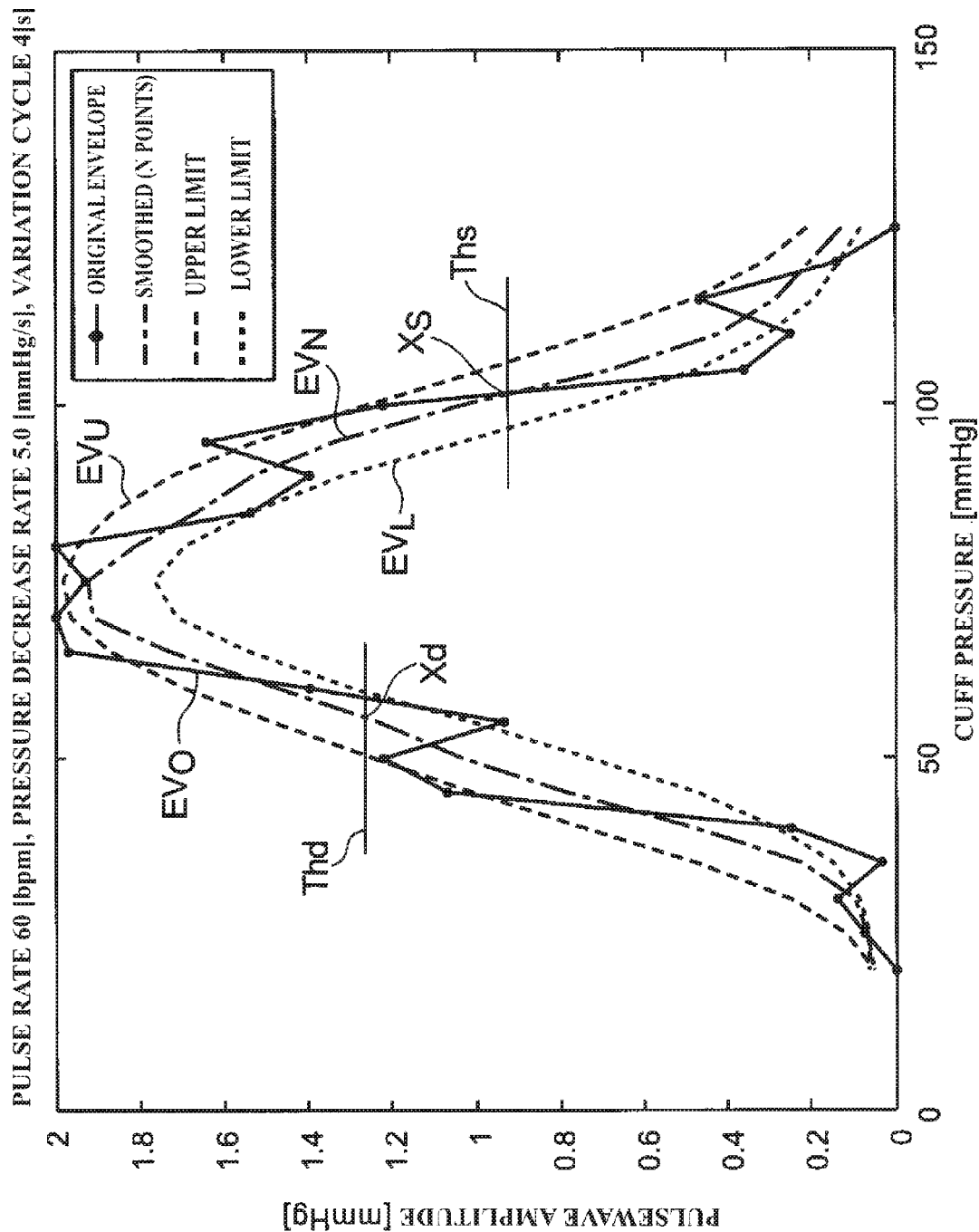
FIG. 13 is a diagram for illustrating blood pressure values calculated using a conventional electronic blood pressure monitor, in the case where the respiratory period is 4 seconds.
Figure 14:
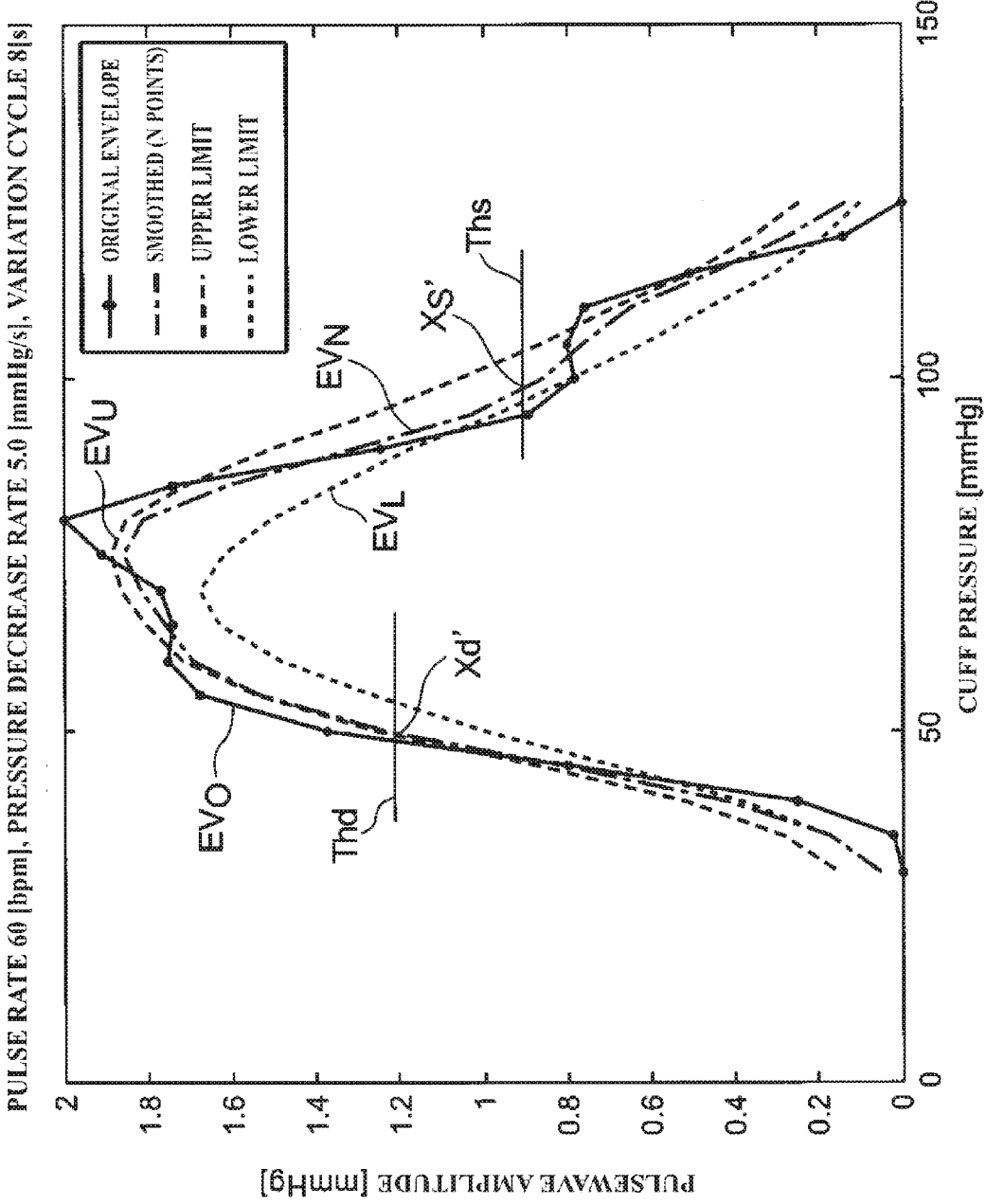
FIG. 14 is a diagram for illustrating blood pressure values calculated using a conventional electronic blood pressure monitor, in the case where the respiratory period is 8 seconds.

Thus, with the singularity removal correction RA, non-periodic components that are different from the respiratory variation and are caused by bodily movement of a measurement subject during blood pressure measurement or the like can be removed from the first envelope EV1. In the subsequent processing, the second envelope EV2 resulting from the singularity removal correction RA is used. Accordingly, the precision of the calculated blood pressure value is increased.

ii) FIG. 12 shows a method of calculating the systolic blood pressure and diastolic blood pressure using the smoothed local-maximum envelope EVmaxS and the smoothed local-minimum envelope EVminS.

As shown in FIG. 10, the smoothed local-maximum envelope EVmaxS and local-minimum envelope EVminS are obtained by carrying out smoothing ALS1 and ALS2, such as a known moving average, on the local-maximum envelope EVmax and the local-minimum envelope EVmin respectively (e.g., JP H05-317274).

After the smoothing ALS1 and ALS2, the threshold level setting unit 66 shown in FIG. 3 calculates and sets the first threshold level Ths' and the second threshold level Thd', which are predetermined percentages of the value of the maximum peak EV2P in the second envelope EV2, as shown in FIG. 12. In this example, similarly to the first example, the first threshold level Ths' is set to be 40% of the value of the maximum peak EV2P, and the second threshold level Thd' is set to be 50% of the value of the maximum peak EV2P. However, modifications such as those stated above can be made.

Next, as shown in FIGS. 10 and 12, the systolic blood pressure calculation unit 67 shown in FIG. 3 obtains two pressure values Pc1' and Pc2' at the points at which portions on the high-pressure-side with respect to the maximum peaks EVmaxSP and EVminSP of the smoothed local-maximum envelope EVmaxS and local-minimum envelope EVminS cross a first threshold value level Ths', and the average value (Pc1'+Pc2')/2 of the two pressure values is calculated as the systolic blood pressure BPsys'. Furthermore, as shown in FIGS. 10 and 12, the diastolic blood pressure calculation unit 68 shown in FIG. 3 obtains two pressure values Pc3' and Pc4' at the points at which portions on the low-pressure-side with respect to the maximum peaks EVmaxSP and EVminSP of the smoothed local-maximum envelope EVmaxS and local-minimum envelope EVminS cross a second threshold value level Thd', and the average value (Pc3'+Pc4')/2 of the two pressure values is calculated as the diastolic blood pressure BPdia'.

In such a case, noise in the two high-pressure-side pressure values Pc1' and Pc2' and in the two low-pressure-side pressure values Pc3' and Pc4' is reduced, and the precision of the calculated blood pressure values (systolic blood pressure BPsys' and diastolic blood pressure BPdia') is increased.

In the second example, processing for performing correction (singularity removal correction) RA in which singularities are removed from the amplitude string AL according to which the first envelope EV1 is created and processing for performing smoothing ALS1 and ALS2 on the local-maximum envelope EVmax and the local-minimum envelope EVmin respectively are both added to the processing of FIG. 4, but there is no limitation to this. It is also possible to add only one of the processes.

In the above-described embodiment, the measurement site was an arm, but there is no limitation to this. The measurement site may be a wrist or a leg.

Also, the electronic blood pressure monitor of the present invention not only measures blood pressure, but may also measure other bodily information such as pulse rate, for example.

The above-described embodiment is merely an example and may be modified in various ways without departing from the scope of the invention.

REFERENCE SIGNS LIST

1 Blood pressure monitor
20 Blood pressure measurement cuff
31 Pressure sensor
50 Display device
100 CPU

The invention claimed is:

1. An electronic blood pressure monitor configured to measure blood pressure at a measurement site using an oscillometric method, the blood pressure monitor comprising:
   a central processing unit (CPU) acting as a cuff pressure control unit that can change pressure in a cuff attached to a measurement site;
   a pressure detection unit comprising a pressure sensor and oscillation circuit, the pressure detection unit configured to detect a cuff pressure signal indicating the pressure in the cuff;
   a pulsewave amplitude string acquisition unit of the CPU configured to retrieve a pulsewave signal that is superimposed on the cuff pressure signal and indicates a pulsewave at the measurement site, and thereby acquire a string of amplitudes indicated by the pulsewave signal;
   a first envelope creation unit of the CPU configured to, with respect to the string of amplitudes acquired by the pulsewave amplitude string acquisition unit, create a first envelope connecting the amplitudes;
   an extremum detection unit of the CPU configured to detect local maxima and local minima in the first envelope;
   a local-maximum envelope creation unit of the CPU configured to, with respect to a string of amplitudes corresponding to the local maxima in the string of amplitudes acquired by the pulsewave amplitude string acquisition unit, create a local-maximum envelope connecting the amplitudes corresponding to the local maxima;
   a local-minimum envelope creation unit of the CPU configured to, with respect to a string of amplitudes corresponding to the local minima in the string of amplitudes acquired by the pulsewave amplitude string acquisition unit, create a local-minimum envelope connecting the amplitudes corresponding to the local minima;
   a threshold level setting unit of the CPU configured to, in order to obtain a systolic blood pressure and a diastolic blood pressure, calculate and set a first threshold level and a second threshold level that are respective percentages determined in advance with respect to a value of a maximum peak of the first envelope;
   a systolic blood pressure calculation unit of the CPU configured to obtain two pressure values at points at which portions on a high-pressure side with respect to maximum peaks of the local-maximum envelope and the local-minimum envelope cross the first threshold level at different times, and calculate an average value of the two pressure values as systolic blood pressure; and
   a diastolic blood pressure calculation unit of the CPU configured to obtain two pressure values at points at which portions on a low-pressure side with respect to maximum peaks of the local-maximum envelope and the local-minimum envelope cross the second threshold level at different times, and calculate an average value of the two pressure values as diastolic blood pressure.

2. The electronic blood pressure monitor according to claim 1, comprising a display device configured to display the calculated systolic blood pressure and diastolic blood pressure.

3. The electronic blood pressure monitor according to claim 1, comprising an envelope correction unit of the CPU configured to correct the first envelope by removing a singularity from the string of amplitudes according to which the first envelope was created.

4. The electronic blood pressure monitor according to claim 1, comprising
   a smoothing unit of the CPU configured to smooth the local-maximum envelope and the local-minimum envelope.

5. The electronic blood pressure monitor according to claim 2, comprising an envelope correction unit of the CPU configured to correct the first envelope by removing a singularity from the string of amplitudes according to which the first envelope was created.

6. The electronic blood pressure monitor according to claim 2, comprising
   a smoothing unit of the CPU configured to smooth the local-maximum envelope and the local-minimum envelope.

7. The electronic blood pressure monitor according to claim 3, comprising
   a smoothing unit of the CPU configured to smooth the local-maximum envelope and the local-minimum envelope.

8. The electronic blood pressure monitor according to claim 5, comprising
   a smoothing unit of the CPU configured to smooth the local-maximum envelope and the local-minimum envelope.

* * * * *